(12) United States Patent
Uji et al.

(10) Patent No.: US 10,098,541 B2
(45) Date of Patent: Oct. 16, 2018

(54) IMAGE PROCESSING APPARATUS

(71) Applicant: CANON KABUSHIKI KAISHA, Tokyo (JP)

(72) Inventors: Akihito Uji, Kyoto (JP); Nagahisa Yoshimura, Kyoto (JP); Hiroshi Imamura, Kawasaki (JP); Makoto Sato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/481,196

(22) Filed: Apr. 6, 2017

(65) Prior Publication Data

US 2017/0296049 A1   Oct. 19, 2017

(30) Foreign Application Priority Data

Apr. 15, 2016  (JP) .................................. 2016-082331

(51) Int. Cl.
| | |
|---|---|
| *A61B 3/14* | (2006.01) |
| *A61B 3/00* | (2006.01) |
| *A61B 3/12* | (2006.01) |
| *G06T 7/90* | (2017.01) |
| *G06K 9/00* | (2006.01) |
| *G06K 9/20* | (2006.01) |
| *G06T 5/00* | (2006.01) |
| *G06T 7/00* | (2017.01) |

(52) U.S. Cl.
CPC .............. *A61B 3/12* (2013.01); *A61B 3/0041* (2013.01); *A61B 3/0058* (2013.01); *A61B 3/14* (2013.01); *G06K 9/0061* (2013.01); *G06K 9/00604* (2013.01); *G06K 9/2081* (2013.01); *G06T 5/003* (2013.01); *G06T 7/0014* (2013.01); *G06T 7/90* (2017.01); *G06T 2207/10024* (2013.01); *G06T 2207/30041* (2013.01)

(58) Field of Classification Search
CPC ........... A61B 3/14; A61B 3/0025; A61B 3/12; A61B 3/102; A61B 3/0058
USPC .................................................. 351/200–246
See application file for complete search history.

(56) References Cited

U.S. PATENT DOCUMENTS

| | | | |
|---|---|---|---|
| 2012/0130270 A1* | 5/2012 | Imamura ............... | G06T 7/0012 600/558 |
| 2015/0366448 A1* | 12/2015 | Iwase ................... | A61B 3/0025 351/206 |

OTHER PUBLICATIONS

Lee, et al., "Detection of Neovascularization Based on Fractal and Texture Analysis with Interaction Effects in Diabetic Retinopathy", PLoS ONE, Dec. 2013, vol. 8, Issue 12, e75699.

* cited by examiner

*Primary Examiner* — Mohammed Hasan
(74) *Attorney, Agent, or Firm* — Canon USA Inc., IP Division

(57) ABSTRACT

An image processing apparatus includes a determination unit configured to determine, as a partial region of a multi-channel fundus image including an optic disk area and a macular area of a subject's eye, one of a region of the multi-channel fundus image which includes the macular area and a region of the multi-channel fundus image which includes the optic disk area, and a generation unit configured to generate an image in which a difference in color of the partial region is enhanced, by applying to the partial region image processing based on a decorrelation stretching method.

33 Claims, 9 Drawing Sheets

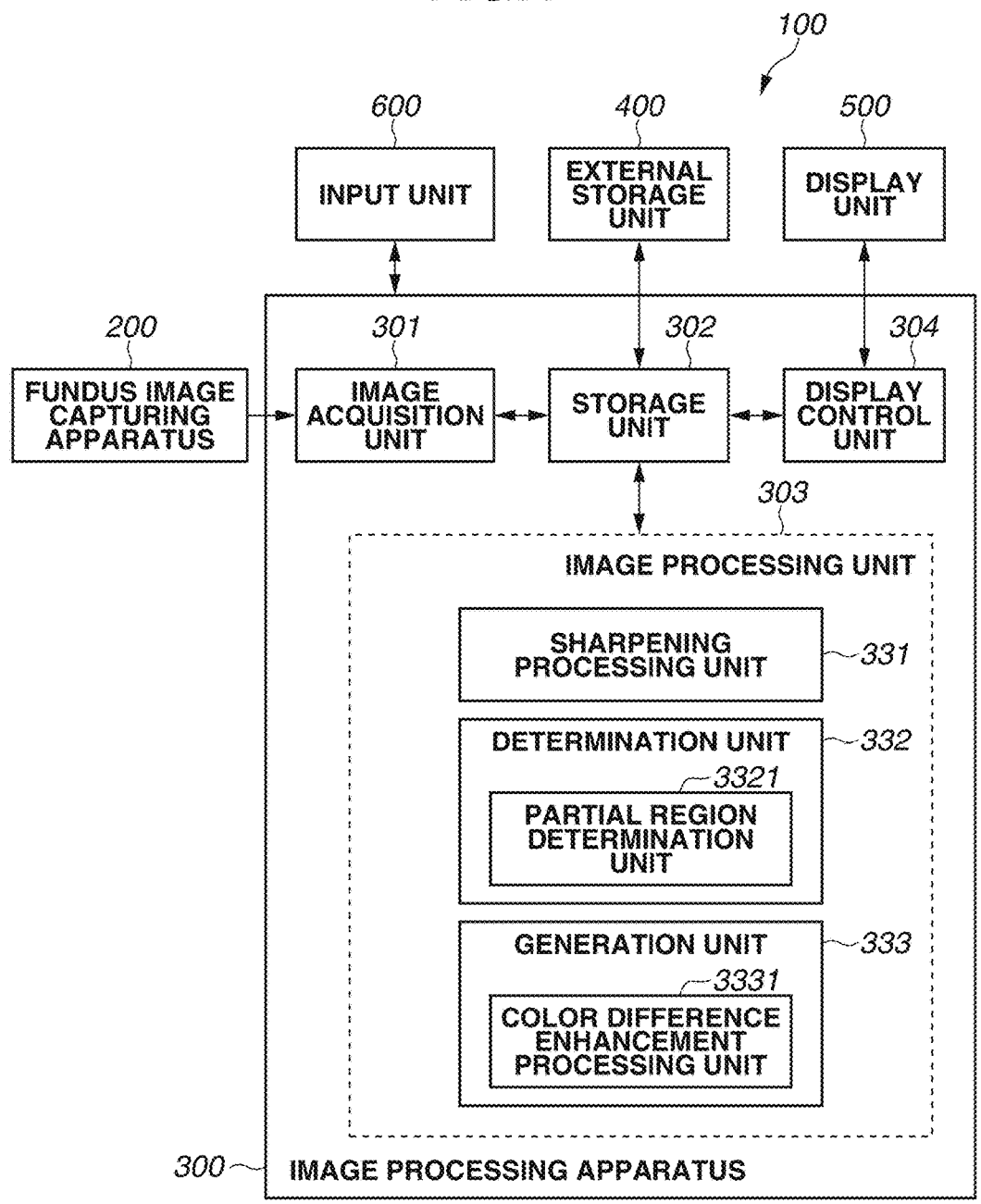

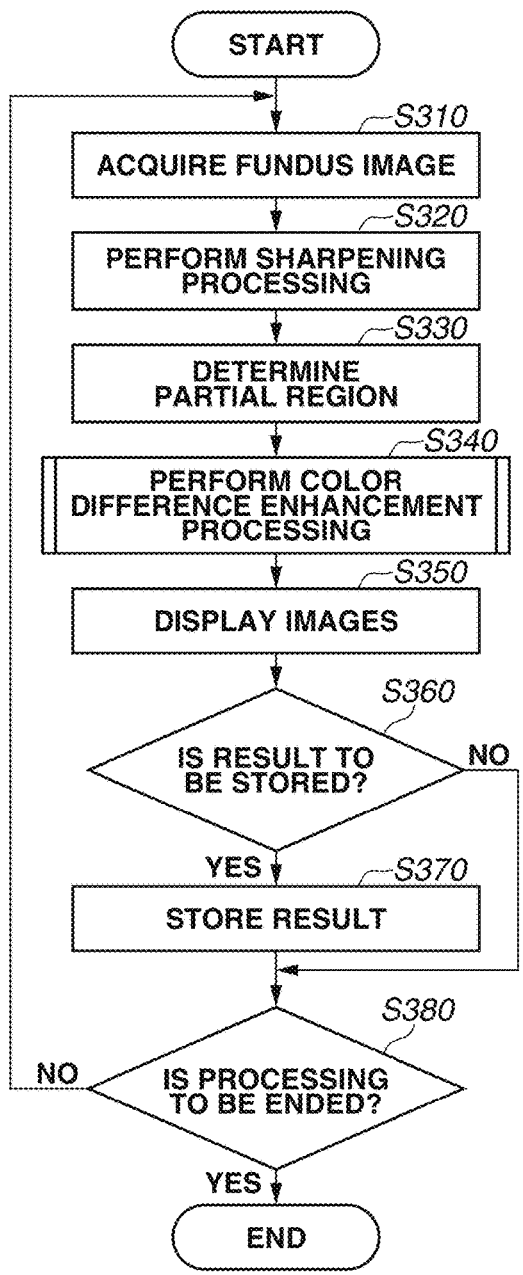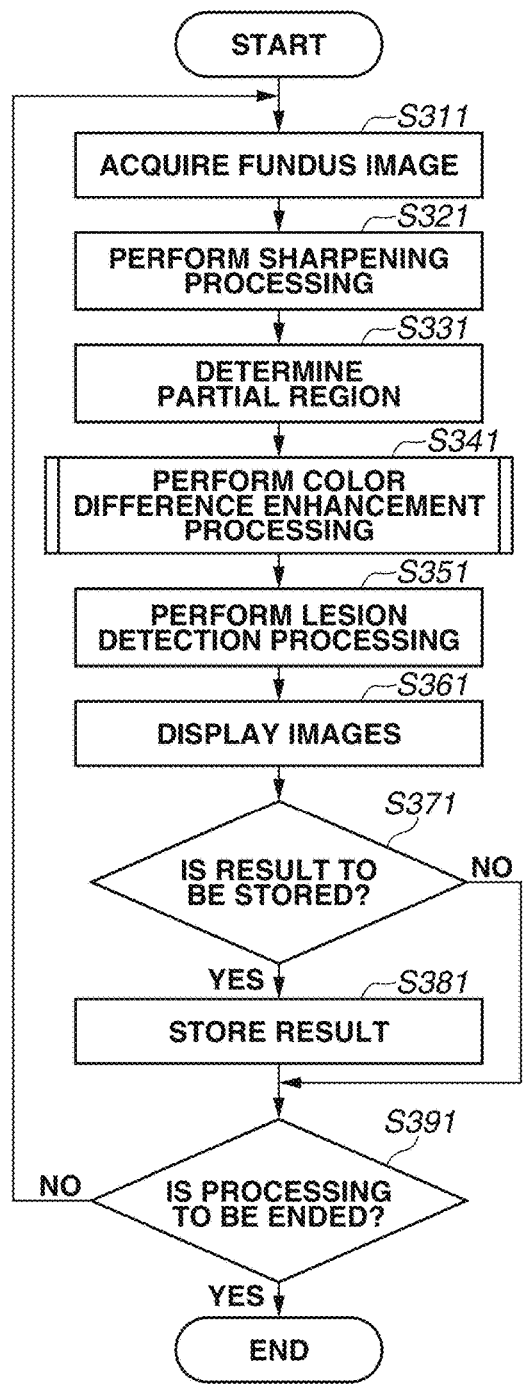

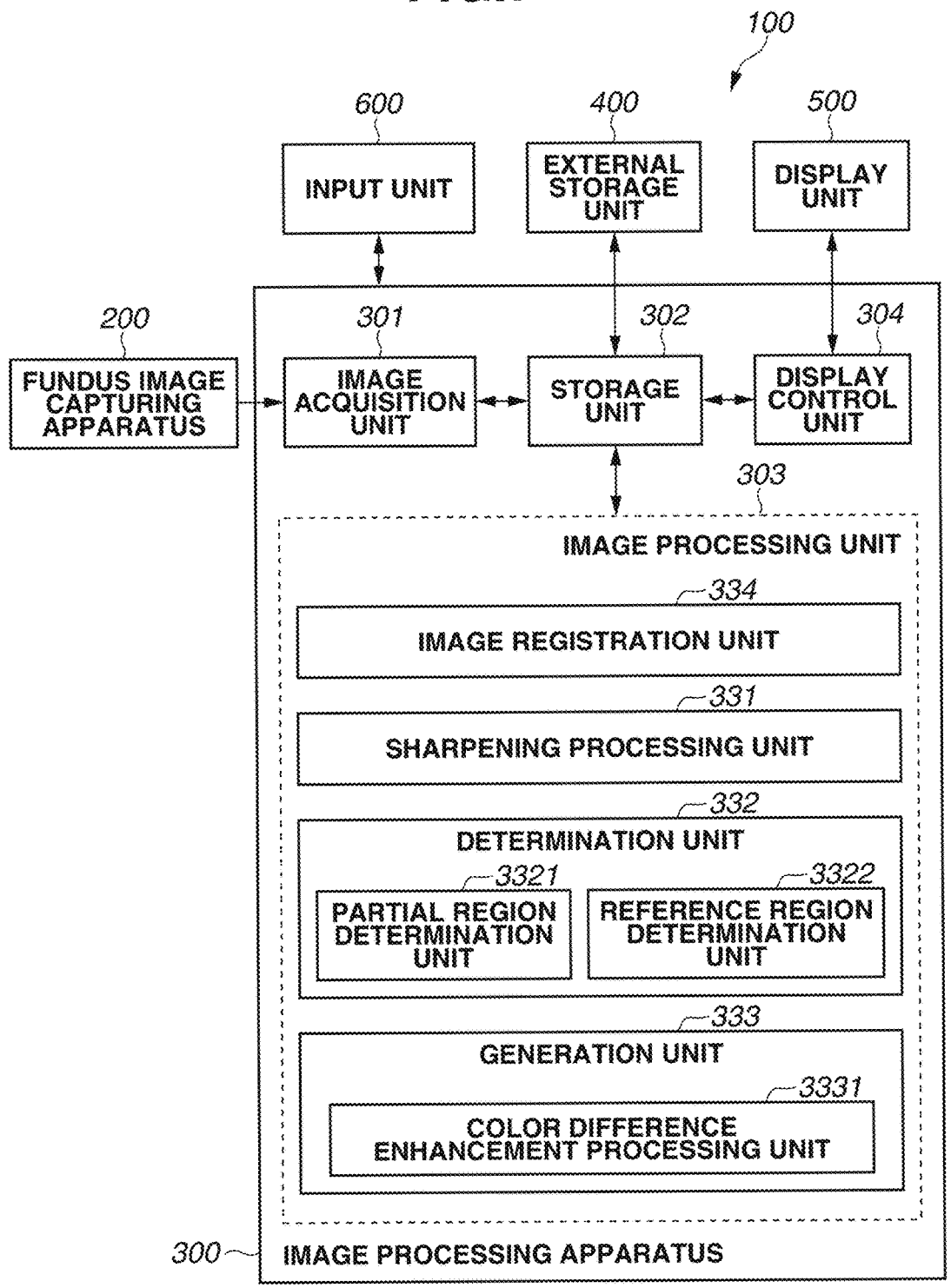

IMAGE PROCESSING APPARATUS

BACKGROUND OF THE INVENTION

Field of the Invention

The present invention relates to an image processing apparatus which performs processing on fundus images.

Description of Related Art

Use of a fundus image capturing apparatus, such as a fundus camera or multi-wavelength scanning laser ophthalmoscope (SLO), enables acquisition of a multi-channel or multi-color image (hereinafter, "color fundus image") in which the state of the fundus is extensively observable. Such fundus image capturing apparatuses are widely used in ophthalmological practice and examination because they are useful for diagnosis of diseases, low in cost, and easy to operate. A color fundus image tends to be reddish entirely and lack variation in color tones compared to general color images. Thus, it is sometimes difficult for ophthalmological specialists to find a low-contrast lesion site (e.g., geographic atrophy in age-related macular degeneration, defect in lamina cribrosa in the optic disk area) from a color fundus image alone.

To increase visibility of an inspection target in a color fundus image, processing of attenuating or deleting components that are unnecessary for the inspection has been performed based on the assumption that red, green, and blue channel components respectively reflect information about the fundus at different depths (blue: retinal surface, green: inside of retina, red: choroid). A red-free image generated by attenuating red component values is one example and is mainly used to enhance the contrast of nerve fibers and retinal vessel regions.

Further, J. Lee et al., "Detection of Neovascularization Based on Fractal and Texture Analysis with Interaction Effects in Diabetic Retinopathy", PLOS ONE, Vol. 8, Issue 12, e75699, 2013, discusses a technique of applying to a color fundus image an image processing method called decorrelation stretching known in the field of remote sensing. In this technique, a decorrelation stretching method is applied to an entire color fundus image as preliminary processing to automatically detect a new blood vessel from the color fundus image of diabetic retinopathy using fractal and texture analysis.

The decorrelation stretching method is known as a process of converting a color image which lacks in color variation into an image which is rich in color tones. Specifically, in the decorrelation stretching method, data with a high correlation between channel components (FIG. 5A) is converted into a representation with a low correlation (FIG. 5B) using principal component analysis and the amounts of dispersion of respective principal components are equalized (FIG. 5D). After the amounts of dispersion of data in axial directions of the respective principal components are stretched to a target amount (FIG. 5E), inverse conversion is performed to convert the image into an image which is richer in color tones (FIG. 5F).

SUMMARY OF THE INVENTION

According to an aspect of the present invention, an image processing apparatus includes an acquisition unit configured to acquire a color fundus image including an optic disk area and a macular area of a subject's eye, a determination unit configured to determine, as a partial region of the fundus image fundus image, one of a region of the fundus image fundus image which includes the macular area and a region of the fundus image fundus image which includes the optic disk area, and a generation unit configured to generate an image in which a difference in color of the partial region is enhanced, by applying image processing based on a decorrelation stretching method to the partial region.

Further features of the present invention will become apparent from the following description of exemplary embodiments with reference to the attached drawings.

BRIEF DESCRIPTION OF THE DRAWINGS

FIG. 1 is a block diagram illustrating a configuration of an image processing system according to a first exemplary embodiment.

FIGS. 3A and 3B are flow charts each illustrating a process which is executed by the image processing system according to the first exemplary embodiment.

FIG. 7 is a block diagram illustrating a configuration of an image processing system according to a second exemplary embodiment.

DESCRIPTION OF THE EMBODIMENTS

Application of a decorrelation stretching method to color fundus images makes it easier for doctors without expensive inspection instruments, such as optical coherence tomographic (OCT) apparatuses, and doctors inexperienced in radiological interpretation of color fundus images to find a low-contrast lesion site even when the lesion site is in an initial state, so inaccuracies in radiological interpretation are expected to decrease.

When decorrelation stretching is applied to an entire color fundus image as in the conventional technique, the following cases can occur. First, there can be a case in which when a luminance range is wide as in an image including a low-luminance macular area and a high-luminance optic disk area, assignment of a different color to a low-contrast lesion site to clearly enhance a color difference cannot be executed. Further, there can be a case in which values of pixels of a high-luminance area, such as the optic disk area, of an image on which decorrelation stretching processing has been performed are saturated. In this case, if a target amount which relates to the amounts of dispersion of data in respective directions of principal components is set to a small amount, no pixel value saturation occurs in any area, but there can be a case in which assignment of a different color to a low-contrast lesion site to clearly enhance a color difference cannot be executed.

An exemplary embodiment of the present invention is directed to a technique of increasing visibility of a low-contrast lesion site in a color fundus image having a wide luminance range, such as a color fundus image which includes an optic disk area and a macular area of an eye to be examined.

Various exemplary embodiments of the present invention will be described in detail below with reference to the drawings.

The following describes a first exemplary embodiment. In the present exemplary embodiment, a case will be described in which an image processing apparatus according to the present exemplary embodiment sets a target region including a macular area with respect to a color fundus camera image of an eye with age-related macular degeneration and performs color difference enhancement processing on the target region using decorrelation stretching to highlight a geographic atrophy lesion. The following describes an image processing system including the image processing apparatus according to the present exemplary embodiment, with reference to the drawings.

Figure 2A:
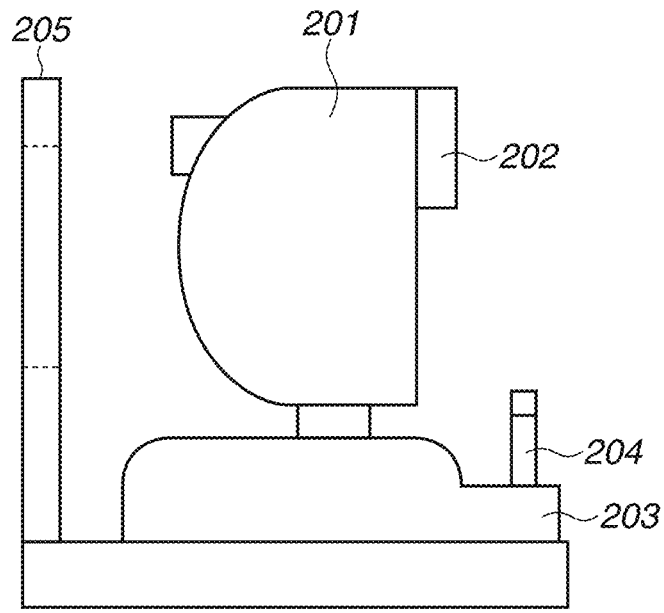
FIGS. 2A and 2B each illustrate a configuration of a fundus image capturing apparatus according to the first exemplary embodiment.

FIG. 1 illustrates a configuration of an image processing system 100 including an image processing apparatus 300 according to the present exemplary embodiment. As illustrated in FIG. 1, in the image processing system 100, the image processing apparatus 300 is communicably connected via an interface to each of a fundus image capturing apparatus 200 (which is an example of an ophthalmological imaging apparatus including an imaging light source configured to generate at least visible light), an external storage unit 400, a display unit 500, and an input unit 600. FIG. 2A is a side view illustrating an example of a configuration of the fundus image capturing apparatus 200. The fundus image capturing apparatus 200 includes a measurement unit 201, a camera unit 202 including an image sensor, a main body portion 203, a joystick 204, and a face-rest 205. Alternatively, the image sensor can be included in the measurement unit 201. Further, while a fundus camera is described as an example of the fundus image capturing apparatus 200 in the present exemplary embodiment, the fundus image capturing apparatus 200 is not limited to the fundus camera. For example, the fundus image capturing apparatus 200 can be an apparatus other than the fundus camera, such as a scanning laser ophthalmoscope (SLO) using a plurality of light sources having different main wavelengths.

The measurement unit 201 includes an optical system which irradiates a subject's eye to be examined with light. The measurement unit 201 further includes an optical system which guides returned light from the subject's eye to the image sensor. The measurement unit 201 is configured to be driven three-dimensionally with respect to the main body portion 203 according to an operation of the joystick 204 by an examiner. Further, the measurement unit 201 is configured to be driven three-dimensionally with respect to the main body portion 203 by a motor controlled by a processor in automatic alignment.

The camera unit 202 includes an image sensor. For example, the camera unit 202 is realized by a main body portion of a single-lens reflex camera. The camera unit 202 can include a display unit capable of displaying captured images and an operation unit such as a touch panel. The camera unit 202 can be attached to the outside of the measurement unit 201 or can be included inside the measurement unit 201.

The main body portion 203 includes, for example, the motor which drives the measurement unit 201 and a mechanism for transmitting to the measurement unit 201 an operation of the joystick 204 by an examiner in the form of power.

The joystick 204 is a member which is used to drive the measurement unit 201. While the joystick 204 is used to drive the measurement unit 201 in the present exemplary embodiment, the member is not limited to the joystick 204. For example, an examiner operation can be received with a touch panel to drive the measurement unit 201 based on the examiner operation.

The face-rest 205 is a member which fixes the face of the subject. The face-rest 205 includes a chin-rest and a forehead-rest. The subject's chin and forehead are fixed by the face-rest 205 to fix the subject's eye to be examined.

Figure 2B:
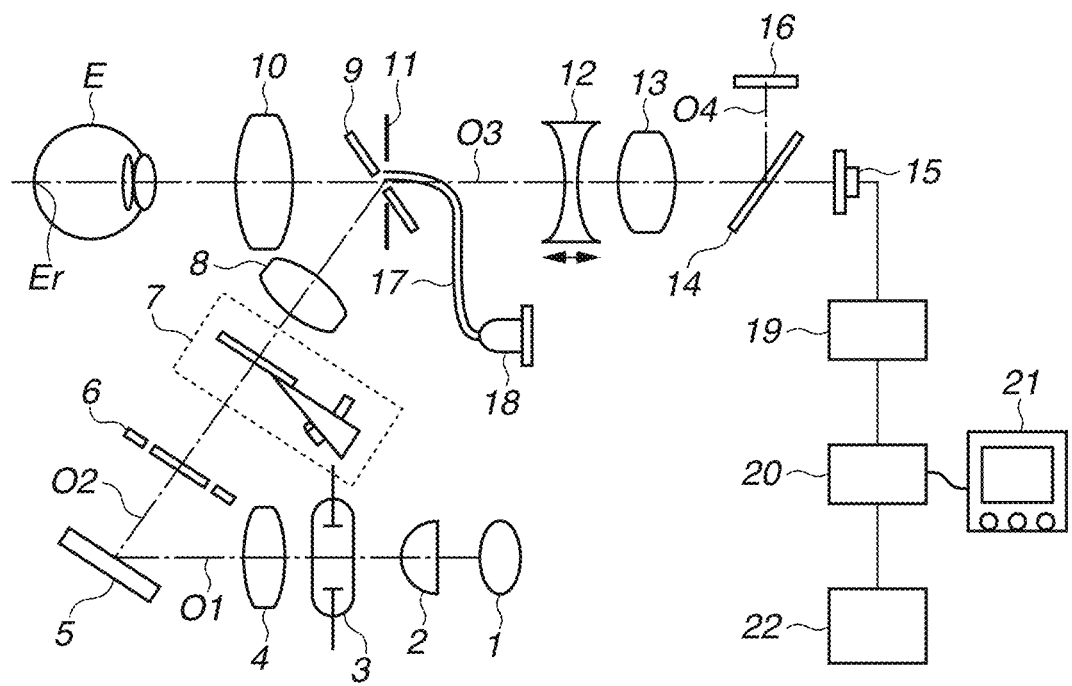

Next, a configuration of the fundus image capturing apparatus 200 will be described in detail below. FIG. 2B illustrates an example of an interior configuration of the measurement unit 201 and the camera unit 202. An illumination optical system is configured on optical axes O1 and O2. On the optical axis O1, an observation light source 1, a condenser lens 2, an imaging light source 3 (e.g., a stroboscopic lamp), a lens 4, and a mirror 5 are disposed. The observation light source 1 includes a light-emitting diode (LED) light source which emits near-infrared light. The observation light source 1 can be a light source other than the LED light source. The imaging light source 3 is realized by, for example, a LED light source or xenon tube and emits, for example, visible light. Further, on the optical axis O2 along a direction in which light emitted from the observation light source 1 is reflected by the mirror 5, a ring diaphragm 6 including a ring-shaped aperture, a focus index projection unit 7, a relay lens 8, and a perforated mirror 9 including a central aperture are serially disposed.

Further, on an optical axis O3 along a direction in which the light emitted from the observation light source 1 is reflected by the perforated mirror 9, an objective lens 10 is disposed to face a subject's eye E to be examined. Further, an imaging diaphragm 11 is provided in a hole portion of the perforated mirror 9, and a focus lens 12, an imaging lens 13, a mirror 14, and an image sensor 15 are serially disposed behind (on a side which is opposite to the eye to be examined E side) the imaging diaphragm 11.

Further, on an optical axis O4 along a direction in which returned light from the subject's eye E is reflected by the mirror 14, an internal fixation lamp 16 is disposed. The internal fixation lamp 16 includes a liquid crystal display panel and a backlight for projecting a fixation target onto an arbitrary position on a fundus Er of the subject's eye E. The internal fixation lamp 16 is disposed in an optically conjugate position with respect to the image sensor 15.

Further, an exit end of a light guide 17 which guides an index light flux is disposed in a position deviated rightward or leftward from the optical axis O3 near the hole portion of the perforated mirror 9. A LED light source 18 for lighting an alignment index is connected to an incident end of the light guide 17, and light emitted from the exit end of the light guide 17 is projected as the alignment index onto the subject's eye E. The image sensor 15 is a sensor which receives returned light from the subject's eye E and is realized by, for example, a charge-coupled device (CCD) sensor. The image sensor 15 is not limited to the CCD sensor and can be realized by, for example, a complementary metal oxide semiconductor (CMOS) sensor. Further, the image sensor 15 has sensitivity with respect to, for example, infrared light and visible light. Alternatively, an image sensor having sensitivity with respect to infrared light and an image sensor having sensitivity with respect to visible light can be included separately. Further, the image sensor 15 is connected to a fundus image generation unit 19. The fundus image generation unit 19 generates a fundus image of the subject's eye E based on output of the image sensor 15 having received returned light from the fundus Er. For example, the fundus image generation unit 19 generates a monochrome image based on light emitted from the observation light source 1 and returned from the subject's eye E, and generates a color image based on light emitted from the imaging light source 3 and returned from the subject's eye E.

The fundus image generation unit 19 can be included in the camera unit 202, the measurement unit 201, or the image processing apparatus 300. The fundus image generation unit 19 is realized by, for example, a processing unit such as a central processing unit (CPU), application specific integrated circuit (ASIC), or field-programmable gate array (FPGA), and the processing unit such as the CPU executes a program stored in a read-only memory (ROM) (not illustrated) to function as the fundus image generation unit 19. Further, the fundus image capturing apparatus 200 includes a control unit 20, a monitor 21, and an operation unit 22.

The image processing apparatus 300 includes an image acquisition unit 301, a storage unit 302, an image processing unit 303, and a display control unit 304. The image acquisition unit 301 is an example of an acquisition unit according to the present exemplary embodiment. The image acquisition unit 301 acquires a multi-channel fundus image (multi-color fundus image) captured by the fundus image capturing apparatus 200 and stores the acquired multi-channel fundus image in the storage unit 302. The image processing unit 303 includes a sharpening processing unit 331, a determination unit 332, and a generation unit 333. The determination unit 332 is an example of a determination unit according to the present exemplary embodiment and includes a partial region determination unit 3321. The generation unit 333 includes a color difference enhancement processing unit 3331.

The external storage unit 400 stores in association with each other information (subject's name, age, sex, etc.) about the subject's eye to be examined, captured image data, image capturing parameter, image analysis parameter, and parameter set by an operator. The input unit 600 is, for example, a mouse, keyboard, or touch operation screen, and the operator gives instructions to the image processing apparatus 300 via the input unit 600. Next, a process which is performed by the image processing apparatus 300 according to the present exemplary embodiment will be described below with reference to FIG. 3A. FIG. 3A is a flow chart illustrating an operation process of the entire system according to the present exemplary embodiment.

<Step S310: Acquisition of Fundus Image>

An subject's eye information acquisition unit (not illustrated) of the image processing apparatus 300 acquires from an external device a subject identification number as information which identifies a subject's eye to be examined. The subject's eye information acquisition unit can include the input unit 600. Further, the subject's eye information acquisition unit acquires information about the eye to be examined which is stored in the external storage unit 400 based on the subject identification number and stores the acquired information in the storage unit 302. The image acquisition unit 301 requests the fundus image capturing apparatus 200 to transfer a fundus image associated with the subject identification number, and acquires the corresponding fundus image from the fundus image capturing apparatus 200. The acquired fundus image is stored in the storage unit 302 (or the external storage unit 400), and in step S350 described below, the fundus image is displayed on the display unit 500. The acquisition of the fundus image by the image acquisition unit 301 is not limited to the transfer from the fundus image capturing apparatus 200, and the image acquisition unit 301 can realize the acquisition by, for example, reading the fundus image stored in the external storage unit 400.

<Step S320: Sharpening Processing>

The sharpening processing unit 331 of the image processing apparatus 300 performs sharpening processing on the fundus image in which a blur occurs due to opacity of an intermediate optic media (crystalline lens or vitreous body). While any arbitrary publicly-known sharpening processing is applicable, the sharpening processing is realized by performing: i) intermediate optic media opacity detection processing and ii) color correction and edge enhancement processing according to the detected opacity in the present exemplary embodiment.

i) In the detection processing, first, a mean value of color information of points of Th % from a bright side of a histogram acquired from a fundus region excluding an optic disk area is determined as highlight point color information. Similarly, a mean value of color information of points of T1% from a dark side of the histogram is determined as shadow point color information. Next, the highlight point color information and the shadow point color information are plotted onto a Y-Cb-Cr space, and a gradient of a line segment connecting the highlight and shadow points in the Cb-axis direction is detected. Further, a contrast (difference in the Y-axis direction) between the highlight and shadow points is also detected.

ii) Rotation processing is performed using the Cr-axis as a rotation axis in such a manner that the detected gradient of the line segment connecting the highlight and shadow points in the Cb-axis direction becomes equal to a gradient in a case of a non-cataract eye. Further, the contrast (difference in the Y-axis direction) between the highlight and shadow points after the rotation processing is also stretched in the Y-axis direction in such a manner that the contrast becomes equal to a contrast in the case of the non-cataract eye. In the present exemplary embodiment, data on the gradient in the Cb-axis direction and contrast value in the case of the non-cataract eye is read in advance from the external storage unit 400 into the storage unit 302 and available for reference.

While any arbitrary publicly-known method is applicable to edge enhancement processing, unsharp masking processing is performed in the present exemplary embodiment.

While the sharpening processing is always performed in step S320 in the configuration according to the present exemplary embodiment, the present exemplary embodiment is not limited to the above-described configuration. For example, a plurality of modes relating to different diagnostic purposes including a cataract mode can be set selectable by a user, and the sharpening processing can be executed on the fundus image if the cataract mode is selected by the user. Further, step S320 can be executed after step S330 described below.

<Step S330: Determination of Partial Region (Partial Region of Fundus Image)>

Figure 4A:
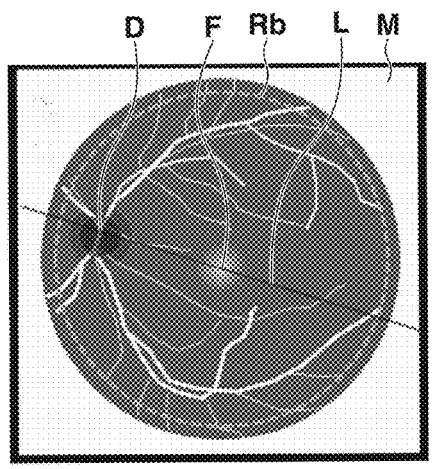
FIGS. 4A, 4B, 4C, 4D, 4E, 4F, and 4G each illustrate a target region which is set in the first exemplary embodiment.

The partial region determination unit 3321 sets with respect to the fundus image sharpened in step S320 a target region on which color difference enhancement processing based on the decorrelation stretching method is to be performed. As illustrated as an example in a luminance profile (FIG. 4E) generated on a white line L in a fundus image (FIG. 4A), an optic disk area D in the fundus image has a high luminance and a wide luminance range, whereas a central fovea F of a macular area has a low luminance. Further, a pixel value in a region M masked by a radiation field diaphragm is zero. Thus, application of the decorrelation stretching method to the entire color fundus image can lead to a case in which assignment of a different color to a low-contrast lesion site of the macular area to clearly enhance a color difference cannot be executed (because many colors are assigned to the optic disk area). Further, saturation of pixel values can occur in the optic disk area, central fovea, etc. in the image on which the decorrelation stretching processing has been performed. In view of the foregoing, the target region is set suitably for an inspection target region and thereafter the color difference enhancement is performed so that more color tones are assigned to subtle changes in pixel values in the inspection target region and saturation of the pixel values in the inspection target region is prevented.

Figure 4B:
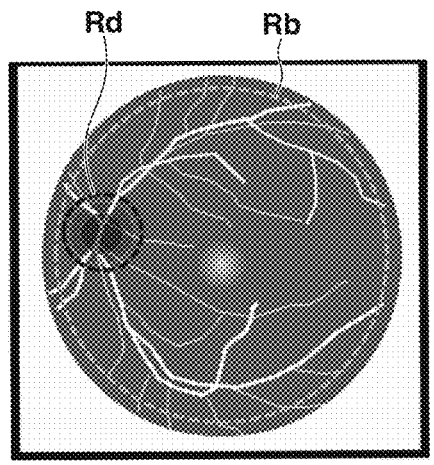
Figure 4C:
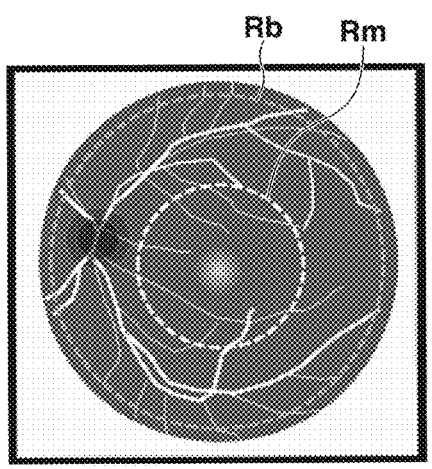

While any arbitrary target region can be set, since the inspection target region is the macula in the present exemplary embodiment, a radiation field (region surrounded by a radiation field Rb and an optic disk area Rd in FIG. 4B) excluding the optic disk area is set as a region including the macular area. Alternatively, a region Rm (FIG. 4C) including the macular area can be set. Further, in a case in which the inspection target region is the optic disk area, the optic disk area Rd (FIG. 4B) can be set as the target region.

Further, in the present exemplary embodiment, the target region is determined by a method in which the user selects the macular area from a list of sites settable as the target region. The present exemplary embodiment is, however, not limited to the above-described method and the determination unit 332 can determine the target region, for example, based on a position on the fundus image that is input to the input unit 600 by the user. Specifically, the determination unit 332 can determine a partial region of the fundus image based on at least one point on the fundus image designated according to a user operation. Alternatively, for example, the modes relating to diagnostic purposes including glaucoma and age-related macular degeneration modes can be set selectable by the user, and the target region can be determined by acquiring a selected mode (age-related macular degeneration in the present exemplary embodiment) from the input unit 600. For example, if the glaucoma mode is selected, the determination unit 332 determines the optic disk area Rd as the target region. If the age-related macular degeneration mode is selected, the determination unit 332 determines the macular area Rm as the target region. Further, the scope of the present exemplary embodiment also encompasses a case in which the determination unit 332 determines the target region based on a lighting position of the fixation lamp 16 used in capturing the fundus image. For example, if the lighting position of the fixation lamp 16 is the central fovea, the macular area Rm is determined as the target area. If the lighting position of the fixation lamp 16 is the optic disk area, the optic disk area Rd is determined as the target region. Further, the partial region determination unit 3321 can determine either one or both of two regions defined by a line intersecting at a predetermined angle with a line segment connecting the optic disk area and the macular area.

Figure 4D:
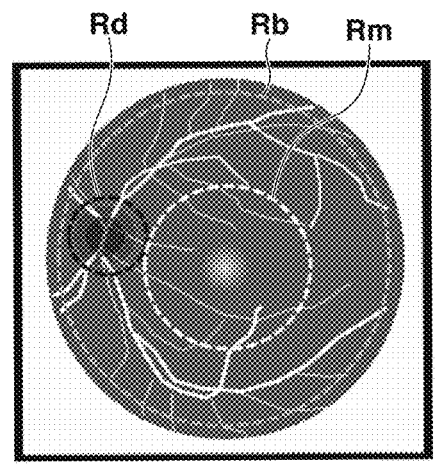
Figure 4E:
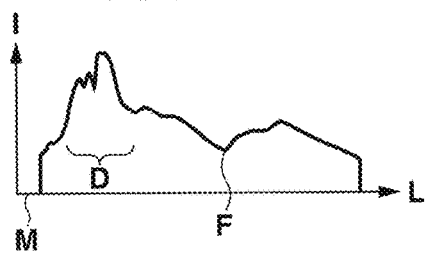

Even in the case in which the inspection target region is the entire fundus image, an application range of the color difference enhancement processing to the fundus image needs to be limited at least to the inside of the radiation field Rb (FIG. 4A). Further, the target region is not limited to one target area, and a plurality of target regions can be set and color difference enhancement processing based on the decorrelation stretching method can be executed on each of the plurality of target regions. For example, as illustrated in FIG. 4D, the optic disk area Rd and the macular area Rm are set, and decorrelation stretching processing can be executed on each of the optic disk area Rd and the macular area Rm so that more colors are set to the optic disk area Rd and the macular area Rm.

<Step S340: Color Difference Enhancement Processing>

The color difference enhancement processing unit 3331 performs color difference enhancement processing based on the decorrelation stretching method on the target region set on the fundus image in step S330. A procedure of decorrelation stretching processing is as follows. After color space conversion is performed, axial directions of principal components are determined by principal component analysis and converted into a low-correlation representation. Next, the amounts of dispersion of the data in the axial directions of the principal components are calculated, and the amounts of dispersion are equalized to decorrelate the data. Next, the amounts of dispersion of the data in the axial directions of the principal components are extended (stretched) to the target amount so that the data is (evenly) distributed in the entire color space. Consequently, the data has richer color tones. Lastly, inverse conversion is performed to return to the original color space (red-green-blue (RGB) space). Details of the color difference enhancement processing based on the decorrelation stretching method will be described below in a description of steps S610 to S650.

<Step S350: Displaying>

The display control unit 304 displays on the display unit 500 the color fundus image acquired in step S310 and the image in which the color differences are enhanced by the decorrelation stretching processing in step S340. At this time, the image in which the color differences are enhanced by the decorrelation stretching method can be displayed next to the fundus image on the display unit 500 or can be superimposed on (placed over) the fundus image. The color difference enhanced image to be displayed on the display unit 500 is not limited to the above-described image. For example, a red-free image that the color difference enhancement processing unit 3331 generates by attenuating red component values of the color fundus image and combining channel data can be displayed on the display unit 500. Specifically, the display control unit 304 can display on the display unit 500 the color difference enhanced image next to an image (image that is different from the color difference enhanced image) obtained by applying image processing that is different from the image processing based on the decorrelation stretching method. In this way, the color fundus image is displayed together with the color difference enhanced image, which is generated by decorrelation stretching, or the red-free image, which is generated by attenuating channel components that are unnecessary for inspection to increase visibility. This enables the user to promptly recognize the presence of a low-contrast lesion site which is easily overlooked. The above-described case is not a limiting case, and scope of the present exemplary embodiment also encompasses a case in which, for example, a plurality of color difference enhanced images generated by applying decorrelation stretching using different values of a parameter used in the decorrelation stretching method used in step S340 is displayed on the display unit 500. In other words, the display control unit 304 can display a first image and a second image next to each other on the display unit 500. The first image is based on a first value of the parameter used in the decorrelation stretching method, and the second image is based on a second value. Examples of the parameter include a parameter which relates to a plurality of axial directions of principal components in a case where pixel values are distributed in a predetermined color space. Examples of the parameter also include a parameter which relates to the target amount in enhancing the amounts of dispersion that are substantially equalized. Examples of the parameter further include the type of the color space. The image processing apparatus 300 according to the present exemplary embodiment desirably includes an analysis unit (not illustrated) configured to extract a predetermined region, such as a lesion site, of the color difference enhanced image by analyzing the color difference enhanced image. At this time, the display control unit 304 desirably displays the extracted predetermined region on the display unit 500 in such a manner that the extracted predetermined region is placed over a position on the fundus image that corresponds to the extracted predetermined region.

<Step S360: Judgment of Whether to Store Result>

The image processing apparatus 300 acquires from an external device an instruction as to whether to store in the external storage unit 400 the plurality of types of color difference enhanced image data including the color fundus image acquired in step S310, the color difference enhanced image to which the decorrelation stretching processing is applied in step S340, and the red-free image displayed in step S350. For example, the instruction is input by an operator via the input unit 600. If a storing instruction is given (YES in step S360), the processing proceeds to step S370. On the other hand, if no storing instruction is given (NO in step S360), the processing proceeds to step S380.

<Step SS370: Storage of Result>

The image processing unit 303 transmits to the external storage unit 400 the examination date, information which identifies the subject's eye to be examined, and data judged to be stored in step S360 in association with each other.

<Step S380: Judgment of Whether to End Processing>

The image processing apparatus 300 acquires from an external device an instruction as to whether to end the series of processing from step S310 to step S370. The instruction is input by an operator via the input unit 600. If an instruction to end the processing is acquired (YES in step S380), the processing is ended. On the other hand, if an instruction to continue the processing is acquired (NO in step S380), the processing returns to step S310, and the processing is performed on another subject's eye to be examined (or the processing is performed again on the same eye to be examined).

Figure 6:
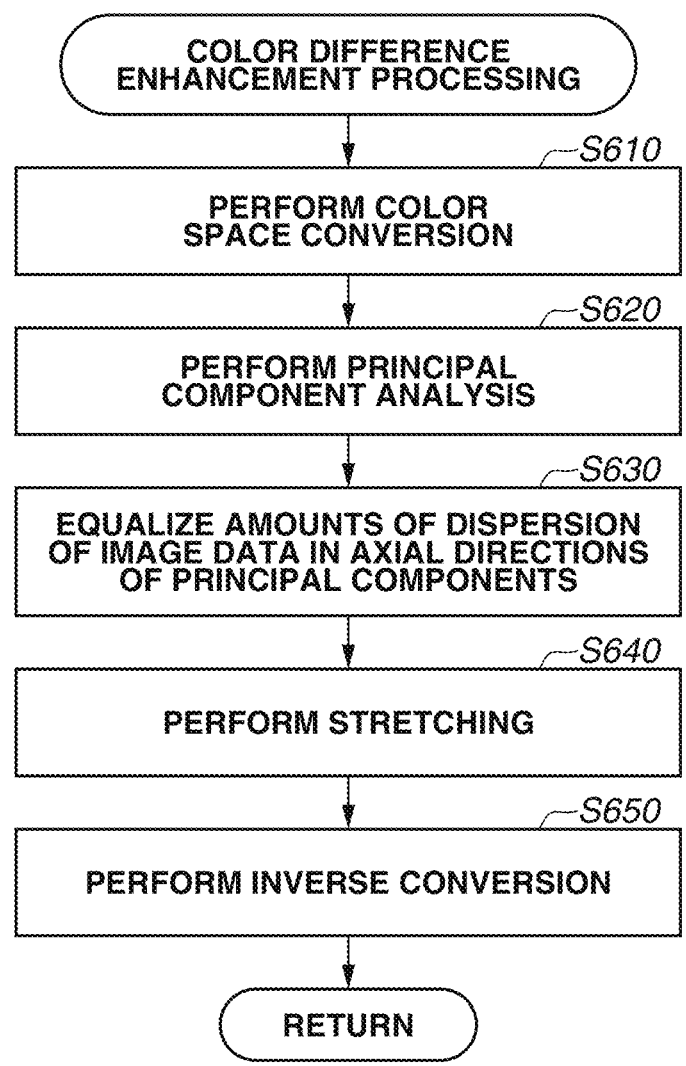
FIG. 6 is a flow chart illustrating details of processing executed in color difference enhancement processing according to the first exemplary embodiment.

The following describes in more detail the processing executed in step S340 (color difference enhancement), with reference to a flow chart illustrated in FIG. 6.

<Step S610: Color Space Conversion>

The color difference enhancement processing unit 3331 converts the color fundus image data into a representation in a different color space. While the color fundus image data can be converted into any arbitrary color space, the color fundus image is converted from the RGB color space into data represented in L*a*b* space in the present exemplary embodiment.

<Step S620: Principal Component Analysis>

Figure 4F:
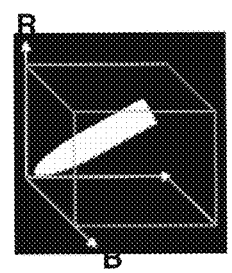
Figure 4G:
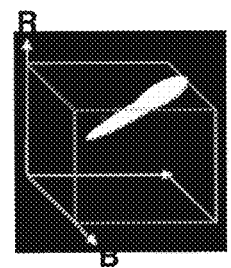
Figure 5A:
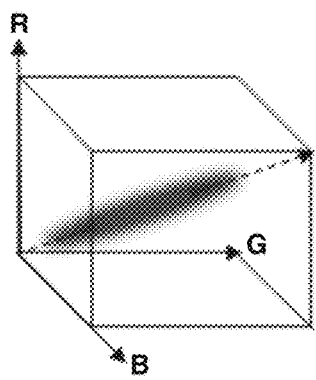
FIGS. 5A, 5B, 5C, 5D, 5E, and 5F schematically illustrate decorrelation stretching processing according to the first exemplary embodiment.
Figure 5B:
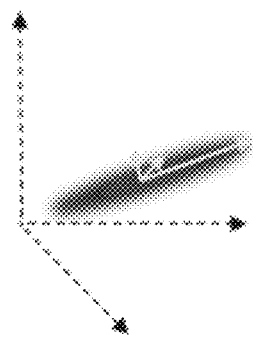

The color difference enhancement processing unit 3331 executes principal component analysis on the partial region of the color fundus image data converted into the representation in the different color space in step S610. An eigenvector and eigenvalue of a variance-covariance matrix are calculated so that the axial directions of the principal components (directions of gray arrows) and the amounts of dispersion (lengths of the gray arrows) of image data in the axial directions of the principal components as illustrated in FIG. 5B can be calculated. The actual calculation is performed on the partial region, so for example in a case in which the region surrounded by the radiation field Rb and the optic disk area Rd in FIG. 4B is set as the partial region including the macular area, the data distribution on the color space is as illustrated in FIG. 4F, and the amount of dispersion in the axial direction of the first principal component is smaller than the amount of dispersion calculated in a case in which the calculation is performed on the entire fundus image. Pixels corresponding to the optic disk region surrounded by the optic disk area Rd are likely to have high R and G values as illustrated in FIG. 4G. While the variance-covariance matrix is used in the principal component analysis in the present exemplary embodiment, the present exemplary embodiment is not limited to the use of the variance-covariance matrix, and the eigenvector and eigenvalue can be calculated using a correlation matrix.

<Step S630: Equalization of Amounts of Dispersion of Data in Axial Directions of Principal Components>

Figure 5C:
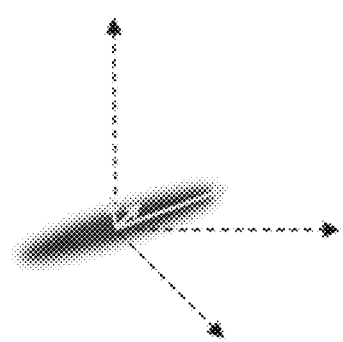
Figure 5D:
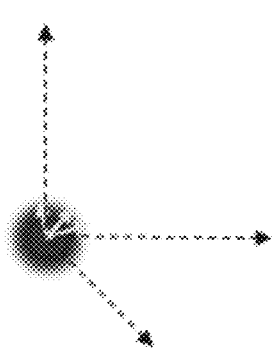

The color difference enhancement processing unit 3331 subtracts offset values from respective pieces of data of the fundus image as illustrated in FIG. 5C, and then equalizes the amounts of dispersion of image data in the respective axial directions of the principal components that are calculated in step S620 (FIG. 5D). In other words, when the pixel values are distributed in the predetermined color space, the amounts of dispersion of color on the plurality of axes of the principal components are substantially equalized. While standard deviation values are calculated as the amounts of dispersion of the image data in the respective axial directions of the principal components in the present exemplary embodiment, this is not a limiting example, and the scope of the present exemplary embodiment also encompasses a case in which, for example, variance values are calculated.

<Step S640: Stretching>

Figure 5E:
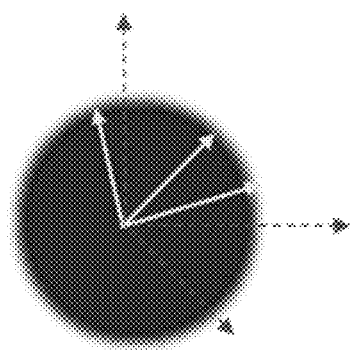
Figure 5F:
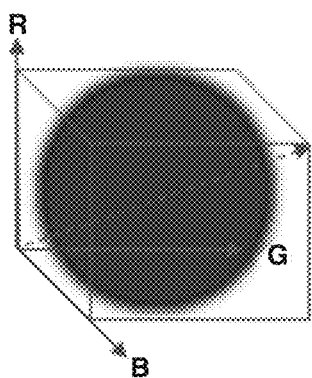

The color difference enhancement processing unit 3331 extends (stretches) the amounts of dispersion of the fundus image data in the predetermined color space which are equalized in step S630 to the target amount, so that the image is converted into a color image in which the color differences are further enhanced, as illustrated in FIG. 5E. FIGS. 5A and 5F are described in RGB color space, and FIGS. A and F are described in L*a*b* space.

<Step S650: Inverse Conversion>

The color difference enhancement processing unit 3331 inversely converts the image data on which the color difference enhancement is performed in step S640 into the original color space (RGB color space in the present exemplary embodiment), and the offset values (mean value) are added thereto so that the fundus image returns to the data representation in the original color space, as illustrated in FIG. 5F. It can be seen that, compared to the image data on which the decorrelation stretching processing is not performed yet (FIG. 5A), the correlations between the channels are decreased and the contrast is enhanced without saturating the pixel values in the color space.

While the case has been described in the present exemplary embodiment in which the image in which the color differences are enhanced by the decorrelation stretching processing is displayed on the display unit 500, the present exemplary embodiment is not limited to the above-described case. For example, the scope of the present exemplary embodiment also encompasses a case in which after color difference enhancement processing based on decorrelation stretching in step S341, lesion detection processing is performed in step S351 based on the image on which the color difference enhancement processing is performed, and the detected lesion region is displayed on the display unit 500 by superimposing the lesion region on the fundus image, as in a process of image processing illustrated in FIG. 3B. An example of the lesion detection is as follows. In the present exemplary embodiment, due to the decorrelation stretching processing limited to the macular area, distances between pixels corresponding to a geographic atrophy region (on the color space) are short. Thus, the detection of the geographic atrophy region can be performed after performing region extension processing on the color difference enhanced image based on a condition that a region is to be extended if the distance on the color space from a pixel corresponding to the central fovea in the color difference enhanced image is smaller than a predetermined value. A boundary of the detected geographic atrophy region is superimposed on the fundus image and displayed on the display unit 500.

In the above-described configuration, the image processing apparatus 300 sets the target region including the macular area with respect to the color fundus image of the eye having age-related macular degeneration, and applies the decorrelation stretching processing to the target region to enhance the difference in color of the low-contrast geographic atrophy lesion. In this way, visibility of the low-contrast lesion site in the macular area in the color fundus image is increased.

The determination unit 332 can determine as the partial region of the fundus image a first region including the macular area of the fundus image and a second region including the optic disk area of the fundus image. In this case, the generation unit 333 can apply respectively different image processing methods based on the decorrelation stretching method to the first and second regions to generate an image in which the respective color differences of the first and second regions are respectively enhanced. In this way, visibility of the low-contrast lesion sites of the macular area and the optic disk area in the color fundus image is efficiently increased.

Figure 8A:
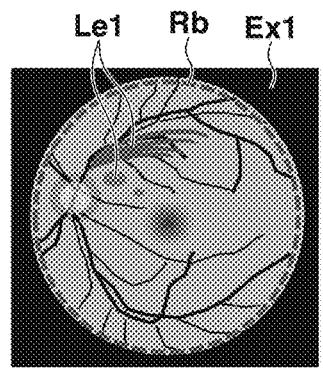
FIGS. 8A, 8B, 8C, 8D, 8E, and 8F illustrate details of image processing according to the second exemplary embodiment.
Figure 8B:
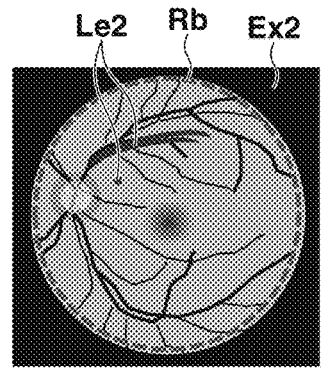
Figure 8C:
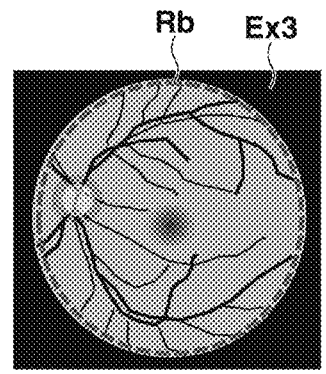

The following describes a second exemplary embodiment. The image processing apparatus according to the present exemplary embodiment captures on different examination dates color fundus camera images Ex1 to Ex3 (FIGS. 8A to 8C) of a subject's eye in which bleeding Le from retinal vessels is observed, and determines as a reference image the latest examination image Ex3 (FIG. 8C) in which the bleeding is stopped. A case will be described in which a target region is set in each of the radiation fields Rb of the examination images Ex1 to Ex3 and a parameter value of the decorrelation stretching processing for the radiation field Rb of the reference image Ex3 is also applied to the radiation fields Rb of the other examination images Ex1 and Ex2 to perform color difference enhancement such that a substantially the same color is assigned to a region that does not change over time.

Figure 9:
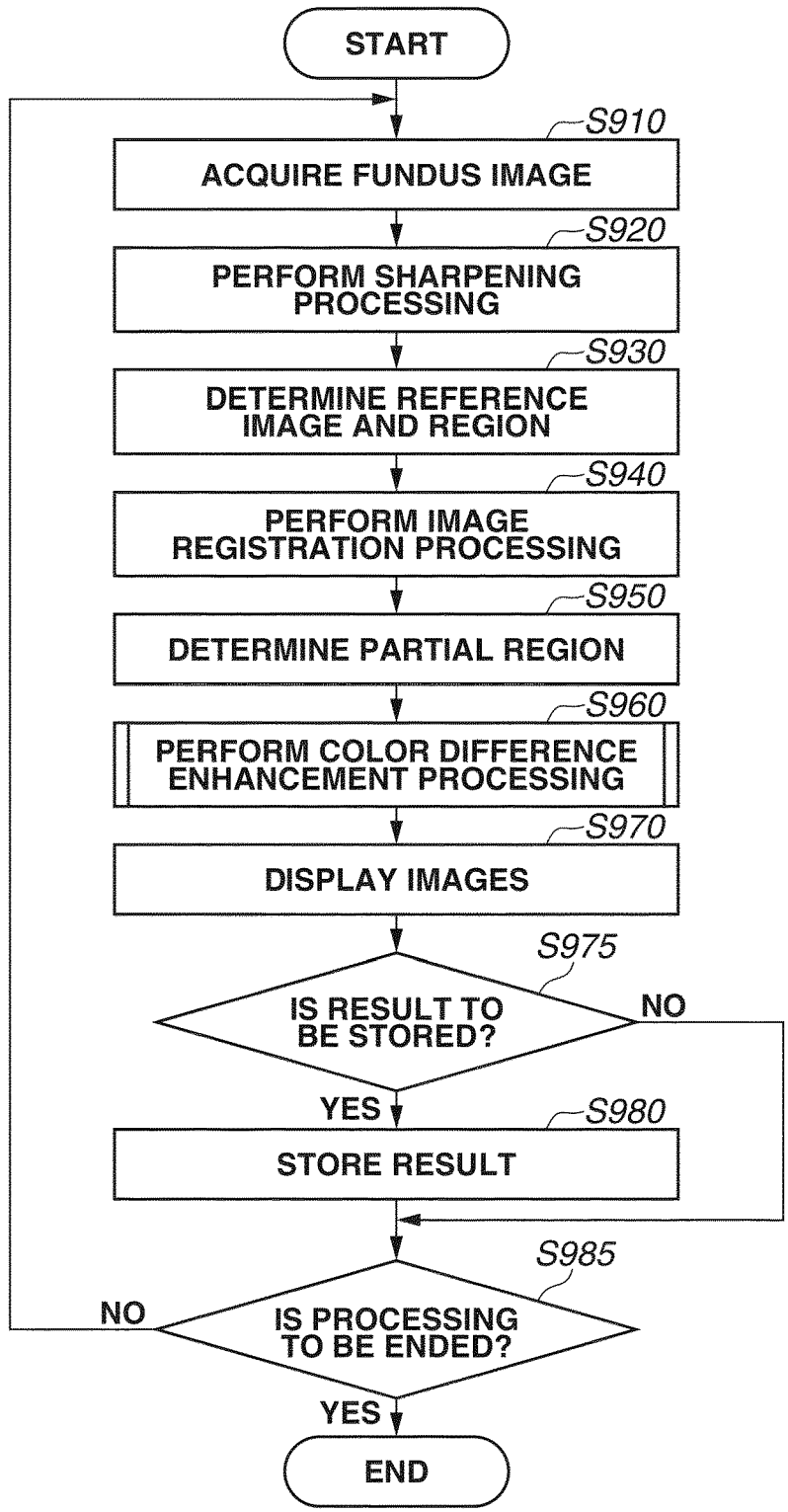
FIG. 9 is a flow chart illustrating a process which is executed by the image processing system according to the second exemplary embodiment.

FIG. 7 illustrates a configuration of the image processing system 100 including the image processing apparatus 300 according to the present exemplary embodiment. The present exemplary embodiment is different from the first exemplary embodiment in that the determination unit 332 includes a reference region determination unit 3322. Further, the process of image processing according to the present exemplary embodiment is as illustrated in FIG. 9. Steps other than steps S910, S930, S940, S950, and S960 are similar to those in the first exemplary embodiment, so description thereof is omitted.

<Step S910: Acquisition of Fundus Image>

The subject's eye information acquisition unit (not illustrated) of the image processing apparatus 300 acquires from an external device a subject identification number and examination date as information which identifies a subject's eye to be examined. The subject's eye information acquisition unit can include the input unit 600. Further, the subject's eye information acquisition unit acquires information about the subject's eye which is stored in the external storage unit 400 based on the subject identification number and stores the acquired information in the storage unit 302. The image acquisition unit 301 requests the fundus image capturing apparatus 200 to transfer fundus images associated with the subject identification number and the examination date, and acquires the corresponding fundus images Ex1 to Ex3 (FIGS. 8A to 8C) from the fundus image capturing apparatus 200. The acquired fundus images are stored in the storage unit 302 (or the external storage unit 400), and in step S970, the fundus images are displayed on the display unit 500. The acquisition of the fundus images by the image acquisition unit 301 is not limited to the transfer from the fundus image capturing apparatus 200, and the image acquisition unit 301 can realize the acquisition by, for example, reading the fundus images stored in the external storage unit 400.

<Step S930: Determination of Reference Image and Region>

The reference region determination unit 3322 determines, from the color fundus images Ex1 to Ex3 of the same eye which are captured on different examination dates and acquired in step S910, a reference image to be used as a reference in image registration and color difference enhancement processing and a partial region corresponding to the reference image. In the present exemplary embodiment, the fundus image corresponding to the latest examination image Ex3 (FIG. 8C) in which the bleeding from the retinal vessels is stopped is determined as the reference image, and the radiation field Rb of the reference image is determined as the partial region. A method of determining the reference image and the region is not limited to the above-described method, and any method can be used. While a publicly-known method can be used as a registration method, registration is performed using affine conversion in the present exemplary embodiment.

<Step S940: Image Registration>

An image registration unit 334 performs image registration processing to register the color fundus images of the same eye which are captured on different examination dates and acquired in step S910, using the image Ex3 determined as the reference in step S930. While a publicly-known method can be used as a registration method, registration is performed using affine conversion in the present exemplary embodiment.

<Step S950: Determination of Partial Region>

The partial region determination unit 3321 sets a target region in each of the examination images registered in step S940. In the present exemplary embodiment, the target region is set in the radiation field Rb. The partial region is not limited to the radiation field Rb and can be, for example, a region including the optic disk area or the central fovea in the center or a region divided in the form of tiles. Further, the partial region is not limited to one region in the fundus image, and a plurality of partial regions can be determined.

<Step S960: Color Difference Enhancement Processing>

The color difference enhancement processing unit 3331 performs color space conversion processing on the reference image determined in step S930 and thereafter performs principal component analysis on the partial region of the reference image to calculate the eigenvector and eigenvalue of the variance-covariance matrix. The eigenvector and eigenvalue calculated for the partial region of the reference image are also applied to the partial regions of the other examination images so that substantially the same color is assigned to the region that does not change over time and visibility of the corresponding lesion region is increased.

The following describes details of the processing executed in step S960, with reference to the flow chart illustrated in FIG. 6. Steps other than steps S620, S630, and S640 in the flow chart illustrated in FIG. 6 are similar to those in the first exemplary embodiment, so description thereof is omitted.

<Step S620: Principal Component Analysis>

Figure 8D:
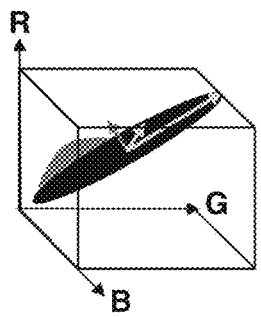
Figure 8E:
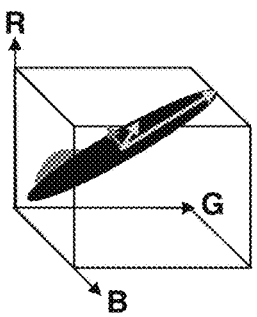
Figure 8F:
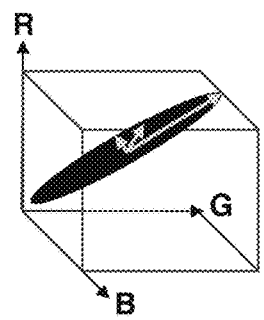

The color difference enhancement processing unit 3331 executes principal component analysis on the partial region of the reference image converted into the representation in the difference color space in step S610. The eigenvector and eigenvalue of the variance-covariance matrix are calculated so that the axial directions of the principal components (directions of gray arrows) and the amounts of dispersion (lengths of the gray arrows) of the image data in the axial directions of the principal components as illustrated in FIG. 8F can be calculated. On the other hand, no principal component analysis is executed on the other examination images, and the eigenvector and eigenvalue (of the variance-covariance matrix or the correlation matrix) calculated for the partial region of the reference image are applied.

If the principal component analysis is executed on the other examination images Ex1 and Ex2 to calculate the axial directions of the principal components and the amounts of dispersion in the axial directions of the principal components and decorrelation stretching processing is performed, a problem below arises. For example, since pixels corresponding to the bleeding region exist as specified by a gray region in FIG. 8D or 8E, the amount of dispersion in the direction of the corresponding principal component is calculated larger (dark gray arrow in FIG. 8D or 8E), so consequently the color difference enhancement effect in the direction of the principal component cannot be expected to be significant as in the case of the reference image. Further, since the axial directions of the principal components are different between the examination images, even if a change in a pixel value is subtle, there is a possibility that a different color is assigned.

<Step S630: Equalization of Amounts of Dispersion of Data in Axial Directions of Principal Components>

The color difference enhancement processing unit 3331 subtracts offset values from data in the partial regions of the examination images and then substantially equalizes the amounts of dispersion in the image data in the axial directions of the principal components using the eigenvector and eigenvalue calculated for the partial region of the reference image in step S620.

<Step S640: Stretching>

The color difference enhancement processing unit 3331 extends (stretches) the amounts of dispersion of the examination image data in the predetermined color space which are substantially equalized in step S630 to the target amount to convert the image data into a color image in which the color differences are enhanced.

In the present exemplary embodiment, the color difference enhancement parameters applied to the partial region of the reference image are also applied to the other examination images so that substantially the same color is assigned to the region that does not change over time. This makes it easy to understand a correspondence relationship between the low-contrast lesion sites on the different examination images, and visibility is further increased.

In the above-described configuration, the image processing apparatus 300 captures on different examination dates the color fundus camera images of the eye in which bleeding from the retinal vessels is observed, and determines the latest examination image as the reference image. The image processing apparatus 300 performs color difference enhancement processing by setting the target region in the radiation field of each of the examination images and applying the parameter values of the decorrelation stretching processing for the radiation field of the reference image to the radiation fields of the other examination images, so that substantially the same color is assigned to the region that does not change over time. In this way, visibility of the low-contrast lesion in the macular area or optic disk area in the color fundus images captured on different examination dates is increased.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-082331, filed Apr. 15, 2016, which is hereby incorporated by reference herein in its entirety.

What is claimed is:

1. An image processing apparatus comprising:
one or more processors; and
memory coupled to the one or more processors and storing instructions, the instructions, when executed by the one or more processors, cause the one or more processors to function as:

an acquisition unit configured to acquire a color fundus image including an optic disk area and a macular area of a subject's eye, the color fundus image being obtained using at least visible light;
a determination unit configured to determine, as a partial region of the color fundus image, one of a region of the color fundus image which includes the macular area and a region of the color fundus image which includes the optic disk area; and
a generation unit configured to generate an image in which a difference in color of the partial region is enhanced, by applying image processing based on a decorrelation stretching method to the partial region.

2. The image processing apparatus according to claim 1, wherein the determination unit determines the partial region based on designation of at least one point on the color fundus image according to a user operation.

3. The image processing apparatus according to claim 1, wherein the determination unit determines the partial region according to a mode relating to a diagnostic purpose selected by a user.

4. The image processing apparatus according to claim 3, wherein in a case where a mode relating to glaucoma is selected, the determination unit determines as the partial region the region of the color fundus image which includes the optic disk area, and in a case where a mode relating to age-related macular degeneration is selected, the determination unit determines as the partial region the region of the color fundus image which includes the macular area.

5. The image processing apparatus according to claim 1, wherein the determination unit determines the partial region according to a site selected by a user.

6. The image processing apparatus according to claim 1, wherein the determination unit determines the partial region according to a position of light incident on the subject's eye from a fixation lamp.

7. The image processing apparatus according to claim 1, further comprising a display control unit configured to display the generated image on a display unit.

8. The image processing apparatus according to claim 1, further comprising a display control unit configured to display the generated image on a display unit in such a manner that the generated image is placed over the partial region of the color fundus image.

9. The image processing apparatus according to claim 1, further comprising:
an analysis unit configured to analyze the generated image to extract a predetermined region of the generated image; and
a display control unit configured to display the extracted predetermined region on a display unit in such a manner that the extracted predetermined region is placed over a position on the color fundus image which corresponds to the extracted predetermined region.

10. The image processing apparatus according to claim 7, wherein the generation unit generates as a different image from the enhanced image an image in which a difference in color of the partial region is enhanced, by applying to the partial region different image processing from the image processing based on the decorrelation stretching method, and
wherein the display control unit displays the enhanced image and the different image next to each other on the display unit.

11. The image processing apparatus according to claim 7, wherein the generation unit generates as the enhanced image a first image and a second image by applying to the partial region image processing based on a first value of a parameter used in the decorrelation stretching method and image processing based on a second value which is different from the first value, and
wherein the display control unit displays the first image and the second image next to each other on the display unit.

12. The image processing apparatus according to claim 1, wherein the acquisition unit acquires a plurality of the color fundus images obtained by capturing images of the subject's eye on different dates,
wherein the determination unit determines a reference fundus image from the plurality of the color fundus images, and
wherein the generation unit applies image processing based on the decorrelation stretching method to another color fundus image among the plurality of the color fundus images which is different from the reference fundus image, using a value of a parameter used in the decorrelation stretching method applied to the partial region of the reference fundus image.

13. The image processing apparatus according to claim 11, wherein the parameter includes at least a parameter relating to a plurality of axial directions of principal components in a case where pixel values of the partial region are distributed in a predetermined color space.

14. The image processing apparatus according to claim 11, wherein in a case where pixel values of the partial region are distributed in a predetermined color space, the generation unit substantially equalizes amounts of dispersion of color on a plurality of axes of principal components, and
wherein the parameter is a parameter relating to a target amount in enhancing the substantially equalized amounts of dispersion.

15. The image processing apparatus according to claim 1, wherein the image processing based on the decorrelation stretching method which is applied to the partial region is processing of substantially equalizing amounts of dispersion of color on a plurality of axes of principal components and enhancing the substantially equalized amounts of dispersion in a case where colors of the partial region are distributed in a predetermined color space.

16. The image processing apparatus according to claim 1, further comprising:
a selection unit configured to select one of a plurality of modes including a cataract mode; and
a sharpening unit configured to sharpen the color fundus image or the partial region in a case where the cataract mode is selected.

17. The image processing apparatus according to claim 1, wherein the determination unit determines, as the partial region of the color fundus image, one of a region of the color fundus image which includes the macular area and does not include the optic disk area and a region of the color fundus image which includes the optic disk area and does not include the macular area.

18. The image processing apparatus according to claim 1, wherein the determination unit determines one of the region which includes the macular area and the region which includes the optic disk area from two regions defined by a line intersecting a line segment connecting the optic disk area and the macular area of the color fundus image.

19. An image processing apparatus comprising:
one or more processors; and memory coupled to the one or more processors and storing instructions, the instructions, when executed by the one or more processors, cause the one or more processors to function as:

an acquisition unit configured to acquire a color fundus image including an optic disk area and a macular area of a subject's eye, the color fundus image being obtained using at least visible light;

a determination unit configured to determine (a) a first region which is a partial region of the color fundus image and includes the macular area and (b) a second region which is a partial region of the color fundus image and includes the optic disk area; and a generation unit configured to generate an image in which a difference in color of the first region and a difference in color of the second region are respectively enhanced, by applying different image processing based on a decorrelation stretching method to the first region and the second region.

20. An image processing apparatus comprising:
one or more processors; and
memory coupled to the one or more processors and storing instructions, the instructions, when executed by the one or more processors, cause the one or more processors to function as:

an acquisition unit configured to acquire a plurality of color fundus images obtained by capturing images of a subject's eye on different dates, the plurality of color fundus images being obtained using at least visible light;

a determination unit configured to determine a reference fundus image from the plurality of color fundus images; and a generation unit configured to generate an image in which a difference in color of the reference fundus image is enhanced and an image in which a difference in color of another color fundus image among the plurality of color fundus images which is different from the reference fundus image is enhanced, by (a) applying image processing based on a decorrelation stretching method to the reference fundus image and (b) applying the image processing based on the decorrelation stretching method to the different fundus image using a value of a parameter used in the image processing based on the decorrelation stretching method which is applied to the reference fundus image.

21. The image processing apparatus according to claim 19, wherein the determination unit determines the partial region based on designation of at least one point on the color fundus image according to a user operation.

22. The image processing apparatus according to claim 19, wherein the determination unit determines the partial region according to a mode relating to a diagnostic purpose selected by a user.

23. The image processing apparatus according to claim 19, wherein the determination unit determines the partial region according to a site selected by a user.

24. The image processing apparatus according to claim 19, wherein the determination unit determines the partial region according to a position of light incident on the subject's eye from a fixation lamp.

25. The image processing apparatus according to claim 19, further comprising a display control unit configured to display the generated image on a display unit in such a manner that the generated image is placed over the partial region of the color fundus image.

26. The image processing apparatus according to claim 19, further comprising:

an analysis unit configured to analyze the generated image to extract a predetermined region of the generated image; and a display control unit configured to display the extracted predetermined region on a display unit in such a manner that the extracted predetermined region is placed over a position on the color fundus image which corresponds to the extracted predetermined region.

27. The image processing apparatus according to claim 20, further comprising:

an analysis unit configured to analyze the generated image to extract a predetermined region of the generated image; and a display control unit configured to display the extracted predetermined region on a display unit in such a manner that the extracted predetermined region is placed over a position on the color fundus image which corresponds to the extracted predetermined region.

28. An image processing method executed in an image processing apparatus comprising one or more processors and memory coupled to the one or more processors and storing instructions, the instructions, when executed by the one or more processors, cause the one or more processors to perform the method comprising:

obtaining a color fundus image including an optic disk area and a macular area of a subject's eye, the color fundus image being obtained using at least visible light;

determining, as a partial region of the color fundus image, one of a region of the color fundus image which includes the macular area and a region of the color fundus image which includes the optic disk area; and generating an image in which a difference in color of the partial region is enhanced, by applying image processing based on a decorrelation stretching method to the partial region.

29. An image processing method executed in an image processing apparatus comprising: one or more processors and memory coupled to the one or more processors and storing instructions, the instructions, when executed by the one or more processors, cause the one or more processors to perform the method comprising:

obtaining a color fundus image including an optic disk area and a macular area of a subject's eye, the color fundus image being obtained using at least visible light;

determining (a) a first region which is a partial region of the color fundus image and includes the macular area and (b) a second region which is a partial region of the color fundus image and includes the optic disk area; and generating an image in which a difference in color of the first region and a difference in color of the second region are respectively enhanced, by applying different image processing based on a decorrelation stretching method to the first region and the second region.

30. An image processing method executed in an image processing apparatus comprising one or more processors and memory coupled to the one or more processors and storing instructions, the instructions, when executed by the one or more processors, cause the one or more processors to perform the method comprising:

obtaining a plurality of color fundus images obtained by capturing images of a subject's eye on different dates, the plurality of color fundus images being obtained using at least visible light;

determining a reference fundus image from the plurality of color fundus images; and generating an image in which a difference in color of the reference fundus image is enhanced and an image in which a difference in color of another color fundus image among the plurality of color fundus images which is different from the reference fundus image is enhanced, by (a) applying image processing based on a decorrelation stretching method to the reference fundus image and (b) applying the image processing based on the decorrelation stretching method to the another color fundus image using a value of a parameter used in the image processing based on the decorrelation stretching method which is applied to the reference fundus image.

31. A non-transitory computer-readable storage medium storing a program for causing a computer to execute the method according to claim 28.

32. A non-transitory computer-readable storage medium storing a program for causing a computer to execute the method according to claim 29.

33. A non-transitory computer-readable storage medium storing a program for causing a computer to execute the method according to claim 30.

* * * * *